United States Patent [19]

Darrow et al.

[11] Patent Number: 4,975,842
[45] Date of Patent: Dec. 4, 1990

[54] ELECTRONIC PATIENT DIARY AND PATIENT MONITORING PROCESS

[75] Inventors: William R. Darrow, Basking Ridge; Robert H. Firman, Maplewood; Harold K. Kushner, West Orange, all of N.J.

[73] Assignee: Schering Corporation, Kenilworth, N.J.

[21] Appl. No.: 231,298

[22] Filed: Aug. 11, 1988

[51] Int. Cl.⁵ ............................................. G06F 15/42
[52] U.S. Cl. ................................................. 364/413.02
[58] Field of Search ...................... 364/413.02, 413.03, 364/569

[56] References Cited

U.S. PATENT DOCUMENTS

| | | | |
|---|---|---|---|
| 3,947,669 | 3/1976 | Simmons et al. | 364/409 X |
| 4,483,346 | 11/1984 | Slavin | 128/710 |
| 4,493,043 | 1/1985 | Forbath | 364/569 |
| 4,518,267 | 5/1985 | Hepp | 368/107 |
| 4,571,698 | 2/1986 | Armstrong | 364/569 |
| 4,652,139 | 3/1987 | Sulcer, Jr. | 368/9 |
| 4,653,022 | 3/1987 | Koro | 364/900 |
| 4,686,624 | 8/1987 | Blum et al. | 364/415 |
| 4,731,726 | 3/1988 | Allen, III | 364/413.09 |
| 4,745,131 | 5/1988 | Yelnosky et al. | 514/596 |
| 4,781,596 | 11/1988 | Weinblatt | 235/472 |

Primary Examiner—Jerry Smith
Assistant Examiner—Steve Kibby
Attorney, Agent, or Firm—Gerald S. Rosen

[57] ABSTRACT

An electronic health care diary is provided for a patient logging data concerning predetermined health conditions, such as for monitoring angina attacks. Upon the onset of e.g. the angina attack the patient presses a start button whereupon a real time clock generates a data and time signal which is stored in a memory along with the fact that the episode started. When the episode is over the patient presses a "stop" switch which generates another date and time signal from the real time clock and stores it in memory along with the fact that the episode terminated. A multi-position switch is actuated by the patient to indicate the extent of the condition, such as the severity of the attack. Optionally, a switch can be provided for correcting a previous erroneous entry, and another switch indicating the time and dosage of any medication. Data logged in the memory can be downloaded through a communications port and programming instructions can be uploaded into the device. An appropriate display provides various messages for the user.

4 Claims, 2 Drawing Sheets

ELECTRONIC PATIENT DIARY AND PATIENT MONITORING PROCESS

FIELD OF THE INVENTION

The present invention relates to an electronic patient diary which is carried by a person suffering from a preselected health condition or illness, or whose health condition is otherwise monitored. The device has no electrical probes or sensors attached to the patient, and the device is adapted to have the patient log on it over a period of time events associated with his condition, and a process for carrying it out.

BACKGROUND OF THE INVENTION

A variety of illnesses manifest themselves through periodic and recurrent episodes of various symptoms. Many of these symptoms are amenable to monitoring through the use of various kinds of machinery. Although the further description of the present invention and its background is made with reference being had mainly to the condition of angina pectoris, it is to be understood that the invention is not restricted to this particular use, but its scope is determined by the claims.

In studying the effect of anti-anginal drugs, one must be aware of the mind set of the Food and Drug Administration and of the expert committees on which it relies in the approval process for such drugs. Anginal pains can be brought on by physical exercise In studying new anti-anginal drugs one primary indicator is the ability of the patient to increase the duration of an exercise between medications, where the increase is brought about by a drug that is being investigated. Thus, the duration of exercise is compared in the case of taking the medication under investigation, with the use of a placebo and/or with a standard reference anti-anginal drug such as propranolol. A patient suffering from angina condition will tolerate only a certain amount of exercise before the onset of the pain. In the case of standard reference anti-anginal drugs the period by which the onset of the pain can be delayed has been well established. The effect of an experimental drug to prolong the exercise period before the onset of pain can, therefore, be compared to the effect without medication, or to when a standard referenced drug is taken. This "exercise-tolerance test" is a difficult, time consuming, and expensive test and, moreover, may not be adequately representative of the actual life conditions under which angina patients exist and for which anti-anginal drugs are intended. Moreover, angina attacks can also occur in the absence of physical exercise, due to emotional stress or other factors which are not addressed by the exercise-tolerance test. Therefore, researchers have employed alternative methods for measuring the efficacy of experimental anti-anginal drugs.

An alternative method involves administering a standard dosage of the experimental anti-anginal drug at standardized intervals of time The patient is permitted to take nitroglycerin tablets between administrations of the experimental drug, whenever angina pain occurs. The reduction of nitroglycerin intake compared to a standardized level of such intake is another indication of the efficacy of the experimental anti-anginal drug. However, exercise tolerance testing is considered by the regulators to be the most important proof of efficacy. Therefore, even if a significant reduction in nitroglycerin consumption can be shown but there is no increase in exercise tolerance, then the new drug would usually not be approved under contemporary acceptance standards of the FDA.

Another method employed by researchers is a handwritten diary by patients recording the date and time of anginal episodes. The FDA and its expert panels are generally reluctant to accept patient diaries, because they were always suspicious about their reliability. It was felt that patients do not start to make handwritten entries into a diary when they experience pain and are just as unlikely to record in writing accurately the end of the pain episode.

Particular difficulties arise in testing the effect of continuously administered nitrate products intended to prevent or reduce the frequency of angina attacks. When exercise tolerance testing is employed, the results can suggest that the active ingredient, as measured by this method, may lose its activity. Tolerance will develop in some patients when nitrate products are administered continuously. At the same time patients do not complain of an increased frequency of episodes. An uncertainty is introduced into the evaluation, because the investigator does not know whether the loss of effect shown by exercise-tolerance testing is realistic, i.e. whether the loss of effect is a phenomenon of the testing system but does not portend lack of effect under the patient's actual lifestyle conditions. Therefore, the exercise tolerance testing may also not really reflect the realities of day-to-day life.

It became clear from the foregoing considerations that a simple device by which angina attacks could be assessed under actual living conditions of patients, would be an ideal way of evaluating anti-anginal drugs, but the prior art which was reviewed provided no guidance in that direction.

U.S. Pat. No. 4,518,267 discloses an event-module for the measurement and study of times, intervals, period, time series and durations. It is a complex device recommended for the treatment of addicts, such as smokers, alcoholics and over-eaters The device is meant to be a therapy support in assisting the patient to fight his habit, rather than a means of diagnosing or evaluating the incidence, severity, and other medical information pertaining to a medical condition such as, for one example, angina. The device is meant to divert the thoughts of the patient by providing him with a game to play. The patient can also enter times and durations of sporting events which he watches, further to divert his attention from his addiction.

U.S. Pat. No. 4,686,624 discloses an apparatus for acquiring and processing data on the dietetics and/or health of a person. The apparatus contains alphanumeric keys for inputting information, window for displaying the information that was introduced and various indications relating to them on the basis of pre-programmed parameters, and a device for selectively refusing inputs. On the basis of the inputs a computer generates instructions for the user of the apparatus from a program, such as what kind of food to eat, or medications to take. The device of the present invention is intended for the purpose of accurately recording patient-generated information pertaining to self-recognized symptoms of a known or suspected disease (e.g. angina pectoris) to facilitate physician or investigator evaluation of the patient's medical condition or response to treatment, under the patient's normal conditions of living.

U.S. Pat. No. 4,653,022 discloses a portable electrocardiogram storing apparatus, a patient actuatable switch, a plurality of electrocardiogram memories, and means for selecting when the switch is actuated, one of the memories for storing the digital signal of an electrocardiogram. The storage also contains timing signals relative to when the cardiogram was taken and stored. The primary purpose of this device, however, is to store information about clinical signs, which may or may not be apparent to the patient.

Also known is a device under the name of Holter monitor. This is a simplified electrocardiographic sensor which provides a single lead tracing over a prolonged period of time. Therefore, it provides a snapshot, as is the case with electrocardiograms. The Holter monitor is designed for recording the onset and frequency and duration of ischemic events, but these do not necessarily correlate with symptomatic angina. The ischemic phenomenon of "silent angina", in which the electrocardiographic changes typical of angina are present but without all the symptoms of an angina attack, is well documented. In such cases electrocardiographic tracing has no corollary in any patient-sensed symptoms, i.e. the patient feels no pain or onset of attack. Furthermore, the Holter monitor does not provide a means for recording the severity of the attack. Another purpose of the Holter monitor is to record electrocardiographic signals over time to track heart arrhythmias, many of which are, like silent angina, not symptomatically apparent to the patient. Furthermore, it is a magnetic recording rather than a graphic strip.

BRIEF DESCRIPTION OF THE INVENTION

It has therefore, occurred to us that the patient diary method of investigation would provide the most ideal results if the diary entry logging could be made more reliable We discovered that upon the onset of pain, frequently accompanied by fear or anxiety, the patient is often not disposed to make a timely written diary entry in a book. In accordance with our present invention, we are providing something convenient for the patient to do promptly and that is to push a button indicating the onset of pain.

Accordingly, we provide the patient with an electronic health care diary for the logging of entries by a patient, which includes means for logging by the patient the onset of a preselected health event, such as the onset of an angina or other pain episode, means for logging the end of the preselected health event, a switch on which the patient can log a qualifying measure of said health event, such as the magnitude or extent of the health event, and a means by which erroneous entries can be corrected. The electronic health care diary of the present invention also includes a real time clock which keeps track of the date and the time of the logging entries made by the patient by any of the preceding means, means for storing the logged entries, a communication port for retrieving the logged data from the diary for analysis, and an electrical storage battery for powering the device. The diary further includes means for logging the time as well as the dosage of medication taken, means for verification of the entries, and an indicator of when battery power is low.

The present invention also includes a process for the logging of events associated with a preselected medical condition such as of episodes of pain in the case of angina attacks, in which the patient logs the onset of the condition, the intensity or extent of the condition, and finally the end of the episode. The patient can further log the time of taking of a drug, as well as the dosage of the drug.

The apparatus and method of the present invention can also be employed in other fields than the development of anti-anginal medications. Accordingly, the apparatus of the present invention permits the capturing of self-scored patient information on the occurrence, frequency, severity, timing, of occurrences, including those that can be correlated to drug dosing, side effects and other treatments even when some other kind of sensing, including automatic sensing, would provide unreliable or otherwise unacceptable results. The apparatus and method of the present invention can, accordingly, be used, for example also for determining the effect of antitussive medications;

determining cough-producing side effects of drugs, such as of angiotensin converting enzyme inhibitors;

assessing the effects of bronchodilators and other anti-asthma treatments;

monitoring sneezing episodes in assessing the efficacy of antihistamines and other anti-allergic agents used for allergic rhinitis; cough cold remedies etc.;

itching attacks in the case of topical dermatologic treatments; for topical or systemic antihistamines; other antipruritic agents; etc.;

drowsiness or the lack thereof, in certain treatments such as with antihistamines, soporifics, etc.;

nausea as a drug induced side effect, or to assess the counteracting effects of antiemetics, antimotion sickness treatments, etc.

DESCRIPTION OF THE DRAWING

Preferred embodiments of the invention are described in greater detail with reference being had to the drawing wherein.

DETAILED DESCRIPTION OF A PREFERRED EMBODIMENT

Figure 1:
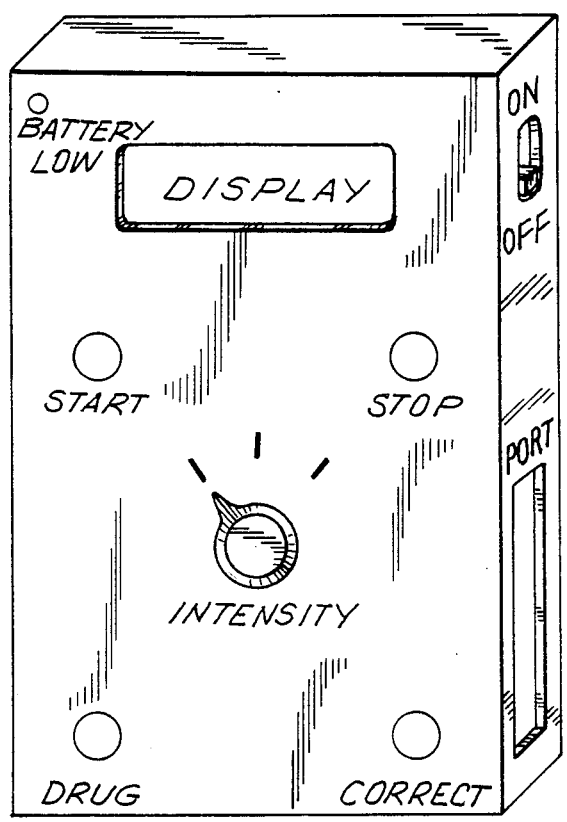
FIG. 1 shows a front perspective view of a preferred embodiment of the present invention.

A preferred embodiment of the apparatus of the present invention, and the method for its use are described with reference to an electronic patient diary device for the monitoring of angina attacks. It is to be understood, however, that the apparatus and its operation are also available for other tasks, as described above. Different legends for the switches, even various overlay templates can be employed, based on any particular use of the device In its simplest form the patient diary for monitoring angina attacks of the present invention is a small box, the same size or hardly larger than a cigarette box as shown in FIG. 1. There is shown on the front of the box, a "battery power low" indicator light, a display for a variety of possible prompts as well as input responses, and some other controls. The display is suitably a liquid crystal display which requires relatively low power and the size of the display depends on the amount of information sought to be displayed, depending on the complexity of the device. The controls include from 2 to 4 pushbuttons and a position switch In the simplest embodiment of the device a "start" and a "stop" button are indispensable for indicating the commencement and the conclusion of an episode. The actuation of either of these pushbutton switches results in the creation of timing signals indicating the date and time of the actuation of the start switch and the date and time of the actuation of the stop switch.

A 3-position switch, suitably a rotary switch, or a sliding switch is to be used by the patient to record a qualifying measure of the episode, such as the intensity or severity of the episode In a somewhat more versatile embodiment of the present invention, a pushbutton switch is provided for generating and recording a timing signal for each occasion when a preselected dose of a predetermined drug is taken. Suitably the number of depressions of this switch closely following each other can serve as an indication of the number of predetermined dosages taken at any given time.

When even greater flexibility of the apparatus is desired, a switch, suitably in the form of a pushbutton, can be provided for the correction of a previously erroneously logged parameter. This can suitably take the form of canceling the last entry. For example, if the patient depressed the "drug" dosing button then changes his mind, he can cancel the same entry by the use of the "correct" button. Depending on ergonomic considerations, that correcting feature can alternatively take the form of a verification. In the latter case, the actuation of any of the other buttons would not be recorded until the actuation of the verification switch confirms the correctness of a previously made conditional entry.

Actuation of the "start" pushbutton not only turns on the power to the device, but also starts a timer which is preset to turn the device off if the patient overlooked to push to "off" button at the end of the episode. The automatic shutoff by the timer can be set to take place suitably after 20 minutes, to accommodate any angina attack of foreseeable duration. If desired, the display can be set constantly to display the date and time such as in 24 hour format, or can be connected to start showing date and time only from the time the "start" button has been actuated Instead, or additionally, the display can show the amount of time elapsed since the "start" button was depressed. Similarly, either the one-time display, if any, and the date and time can be turned of±from the display upon the depression of the "off" button, or upon the expiration of the preset timer interval, whichever is sooner.

The "drug" dose switch can also be adapted to turn the unit power on for a predetermined period, such as 30 seconds. This capability is for the purpose of recording drug dosing even if that takes place at a time when there is no anginal episode taking place.

The grading of the intensity of the attack by the 3-position switch should suitably take place at the end of the episode. The ability subjectively to evaluate the intensity of the pain at the beginning of the episode is likely to be skewed by an exaggeration of the subjective response due to the immediacy of the onset After the episode is over, the evaluation can be done more objectively in a retrospective fashion. Accordingly, the first actuation of the "stop" switch in the preferred embodiment of the invention will not turn the power off to the device, but merely record the date and time of the conclusion of the pain episode. The patient then has an opportunity to adjust the 3-position switch according to whether the pain during the preceding episode was mild, moderate, or severe. A second depression of the "stop" switch will then result in the recording of the setting of the intensity switch at that point. The position of the intensity switch at an any other time can be ignored by the apparatus. Of course, actuation of the "correct" switch can be used to cancel any of the immediately preceding settings or switch actuations Suitably an additional timer can be provided to preserve battery life and to allow a predetermined period, such as 30 seconds, to lapse between the two depressions of the "stop" button. Alternatively, the timer for recording the overall duration of the episode, can be set not to shut off right away if the recording process is deliberately stopped, but to continue timing after the first depression of the "stop" button and to power off the device automatically only if the second depression of the "stop" button did not take place.

As shown in FIG. 1, if desired, a recessed on/off switch can be provided to turn off all power to the device. Alternatively, an on/off switch may be considered undesirable for some purposes. On the side of the apparatus under the power on/off switch, a communication port is provided for connecting the device to an external computer for downloading any recorded data from the device also for uploading program instructions to the device. If a rechargeable battery is used then unused pins of the communication port connectors can be optionally used for recharging the storage battery Alternatively, if desired, a separate recharging jack (not shown) can be provided with a charger to be attached through a standard recharging connection.

The display can be used in a number of ways. The failure of a preselected display to appear on the depression of the "start" button, such as date and time and/or episode timing and/or a word like "onset" or "start" can be used to indicate to the patient that the "start" switch was activated and the device is operational Failure of appearance of the preselected message would indicate that the device is not operational.

A message such as "memory is full" can be used to indicate that the device cannot store any additional data and the device should be turned in for downloading the records.

After the initial depression of the "stop" switch, a message such as "select level now" can be made to appear to prompt setting of the 3-position switch After a switch setting has been made in response to the prompt, words indicating the selected level, such as "mild", "moderate", or "severe" would appear and stay displayed until either the "stop" button is depressed or a timer turns the power off.

A message such as "drug dosing" can be made to appear when the drug dosage button was activated.

After the depression of the "correct" button, a message prompting the selection of a new parameter, based on the parameter that was just canceled, can appear in the display. This message can alternate with an indication of which parameter was just canceled.

A message such as "time out" can be made to appear to indicate that the internal timer will turn the power off due to the lack of patient action.

Suitably power can be supplied to the device by four 1.5 volt nickel-cadmium storage batteries of 500 ma/hrs capacity. About 265 ma/hrs are estimated to be required for a three week period of angina monitoring. This is based on an assumption that there will be an average of approximately 10 episodes a day of about 10 minutes duration.

Figure 2:
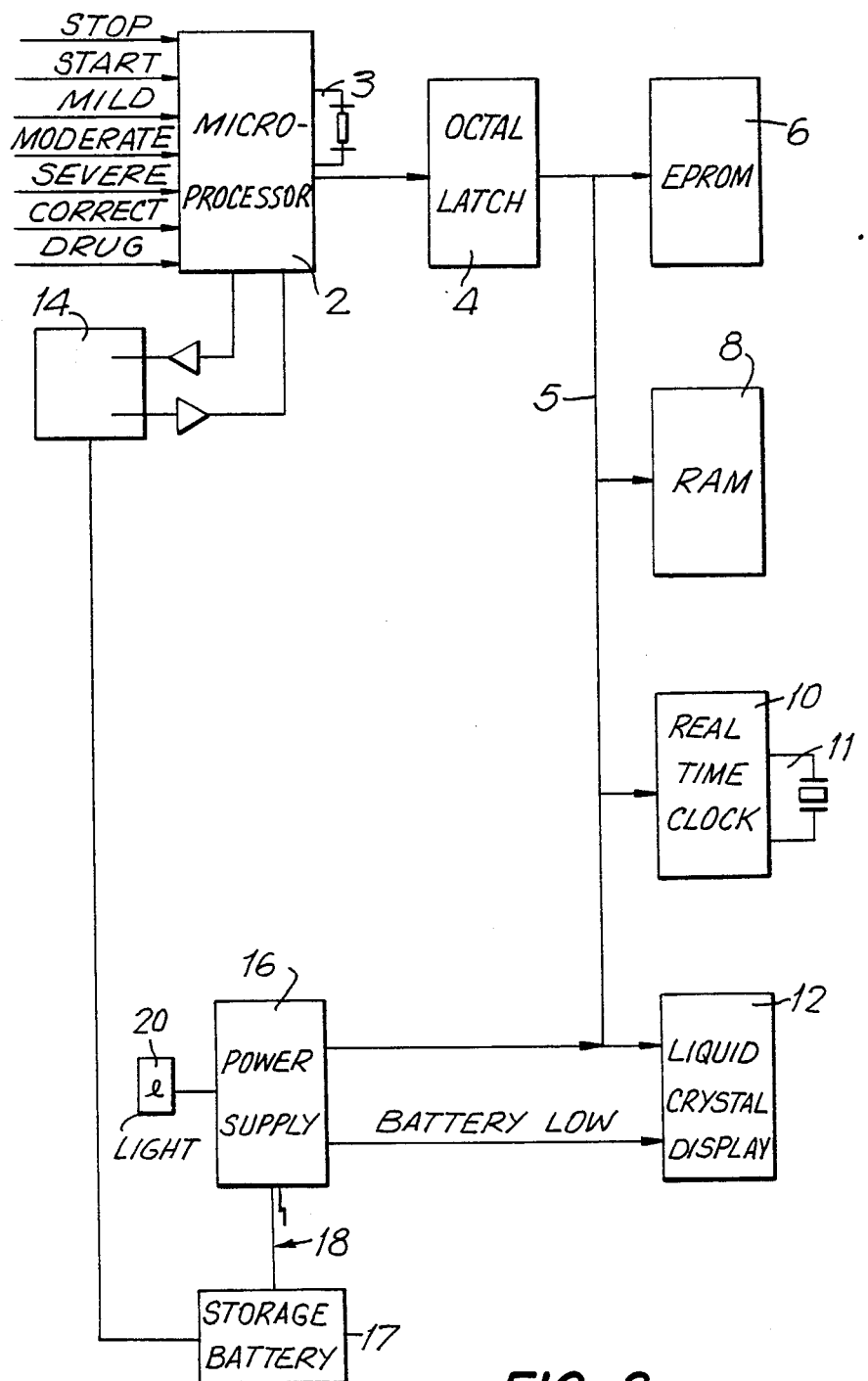
FIG. 2 is a schematic block diagram of a preferred embodiment of the present invention.

FIG. 2 is a block diagram of a preferred embodiment of the device of the present invention. The signals from the "start", "stop", "intensity", "drug" and "correct" switches as shown in FIG. 1, are introduced into a microprocessor 2. This integrated circuit can suitably be one manufactured by Intel Corp., and sold under the designation 80C31BH. A timing crystal 3 provides the clock for the microprocessor. This can be suitably selected to resonate at 3.686 MHz. The microprocessor 2 is connected to an octal latch 4 for receiving an address latch enable signal from the microprocessor and strobe it until another address latch enable is received, and then sends it into the bus 5 of the device. The octal latch can suitably be a unit manufactured by the Harris Co. and sold under the trade designation CP82C82.

A programmable memory (PROM), or an erasable programmable memory (EPROM) 6 is connected to the bus 5 for storing the program functions for any given application of the device, such as angina monitoring. Suitably, ar 8K×8 EPROM chip sold by Intel Corp. under the trade designation 27C64-25 can be used for this purpose.

The next device connected to the bus is a random access memory (RAM) for storing logged information particulars according to the program instructions stored in the EPROM 6. Suitably a memory chip sold by Dallas Semiconductors under the trade designation DS1220AD can be used for this purpose. Advantageously, a separate battery (not shown) can be provided for the random access memory 8 to guard against the volatility of the stored data in case of a loss of power.

The next device shown connected to the bus is a real time clock 10 for supplying date and time information to the RAM 8 upon each logging event by the patient, in accordance with the program instructions stored in the EPROM 6. Suitably, the real time clock/calendar unit can be one sold by Dallas Semiconductors under the trade designation DS1287. Advantageously the backup battery used for the RAM 8 can also be used to maintain the real time clock 10 to continue its function under adverse power conditions, or a separate battery (not shown) for the RAM and another separate battery (not shown) for the real time clock can be provided for that purpose.

Finally a liquid crystal display (LCD) 12 is connected to the bus for providing the display. Suitably, a one line LCD module to accommodate 16 characters can be employed, such as is sold by Epson Corp. under the trade designation EA-X16017AR.

External signals can be introduced to the microprocessor and signals from the device can be withdrawn through the microprocessor via a communication port 14, such as an RS-232C serial port for connection to an external device.

A power supply 16 with a storage battery 17 is adapted to provide power to the entire system. An optional on/off switch 18 as also shown in FIG. 1, can be used to switch the main power supply. When the switch 18 is off, the backup battery or batteries (not shown) maintain(s) the data in the memory 8 and continue(s) operation of the real time clock 10.

If the storage battery runs low, a lamp or a light emitting diode 20 can be suitably provided to give an indication on the front panel of the device that the battery needs recharging. Alternatively, a low power condition of the battery can also be indicated on the LCD 12.

If desired, the storage battery 17 can be recharged through inactive leads of the communication port 14.

We claim:

1. A portable electronic health care diary, adapted to be carried about by the patient, for recording the duration and characteristics of periodic health condition episodes, such as angina attacks, which comprises
    (a) a microprocessor system including an accessible memory and a continuous clock/calendar,
    (b) first patient-operable control means adapted when actuated by the patient to cause said microprocessor to record in said memory an "onset" code, including the time and date of such actuation,
    (c) second patient-operable control means adapted when actuated by the patient to cause said microprocessor to record in said memory a "termination" code, including the time and date of such actuation,
    (d) third patient-operable control means effective only after operation of said second control means and adapted when actuated by the patient to cause said microprocessor to generate and record in said memory an additional code signifying the patient's subjective evaluation of the characteristics of the episode recorded by said "onset" and "termination" codes,
    (e) means providing for periodic retrieval of the data recorded in said accessible memory to enable analysis of the timing, frequency and characteristics of said episodes,
    (f) said third patient-operable control means comprising an adjustable element for generating a signal indicating characteristics of the episode and switch-type control means for causing said microprocessor to record said characteristics.

2. Apparatus according to claim 1, further characterized by
    (a) said last-mentioned switch-type control means comprising said second patient-operable control means, and
    (b) circuit means operable when said second patient-operable control means is actuated in succession, first to cause said microprocessor to record termination of the episode and second to cause said microprocessor to record the characteristics thereof as determined by said adjustable element.

3. A portable electronic health care diary, adapted to be carried about by the patient, for recording the duration and characteristics of periodic health condition episodes, such as angina attacks, which comprises
    (a) a microprocessor system including an accessible memory and a continuous clock/calendar,
    (b) first patient-operable control means adapted when actuated by the patient to cause said microprocessor to record in said memory an "onset" code, including the time and date of such actuation,
    (c) second patient-operable control means adapted when actuated by the patient to cause said microprocessor to record in said memory a "termination" code, including the time and date of such actuation,
    (d) third patient-operable control means, including a patient-adjustable element, effective only after operation of said second control means and adapted when actuated by the patient to cause said microprocessor to record in said memory an additional code signifying the patient's subjective evaluation of the characteristics of the episode recorded by said "onset" and "termination" codes,
    (e) means providing for periodic retrieval of the data recorded in said accessible memory to enable analysis of the timing, frequency and characteristics of said episodes, (f) said microprocessor including delay circuit means enabling operation of said third patient-operable control means only during a brief time period immediately following actuation of said second patient-operable control means.

4. A portable electronic health care diary, adapted to be carried about by the patient, for recording the duration and characteristics of periodic health condition episodes, such as angina attacks, which comprises (a) a microprocessor system including an accessible memory and a continuous clock/calendar, (b) first patient-operable control means adapted when actuated by the patient to cause said microprocessor to record in said memory an "onset" code, including the time and date of such actuation, (c) second patient-operable control means adapted when actuated by the patient to cause said microprocessor to record in said memory a "termination" code, including the time and date of such actuation, (d) adjustable patient-operable control means effective after operation of said second control means and adapted when actuated by the patient to cause said microprocessor to record in said memory an additional code signifying the patient's subjective evaluation of the characteristics of the episode recorded by said "onset" and "termination" codes, (e) means providing for periodic retrieval of the data recorded in said accessible memory to enable analysis of the timing, frequency and characteristics of said episodes, (f) said first patient-operable control means including means for initiating a "power on" condition of said microprocessor, (g) said second patient-operable control means including means for initiating a "power off" condition of said microprocessor, (h) said microprocessor including timer means for delaying said "power off" condition for a period sufficient to enable recording of said subjective evaluation.

* * * * *